Figure 1:
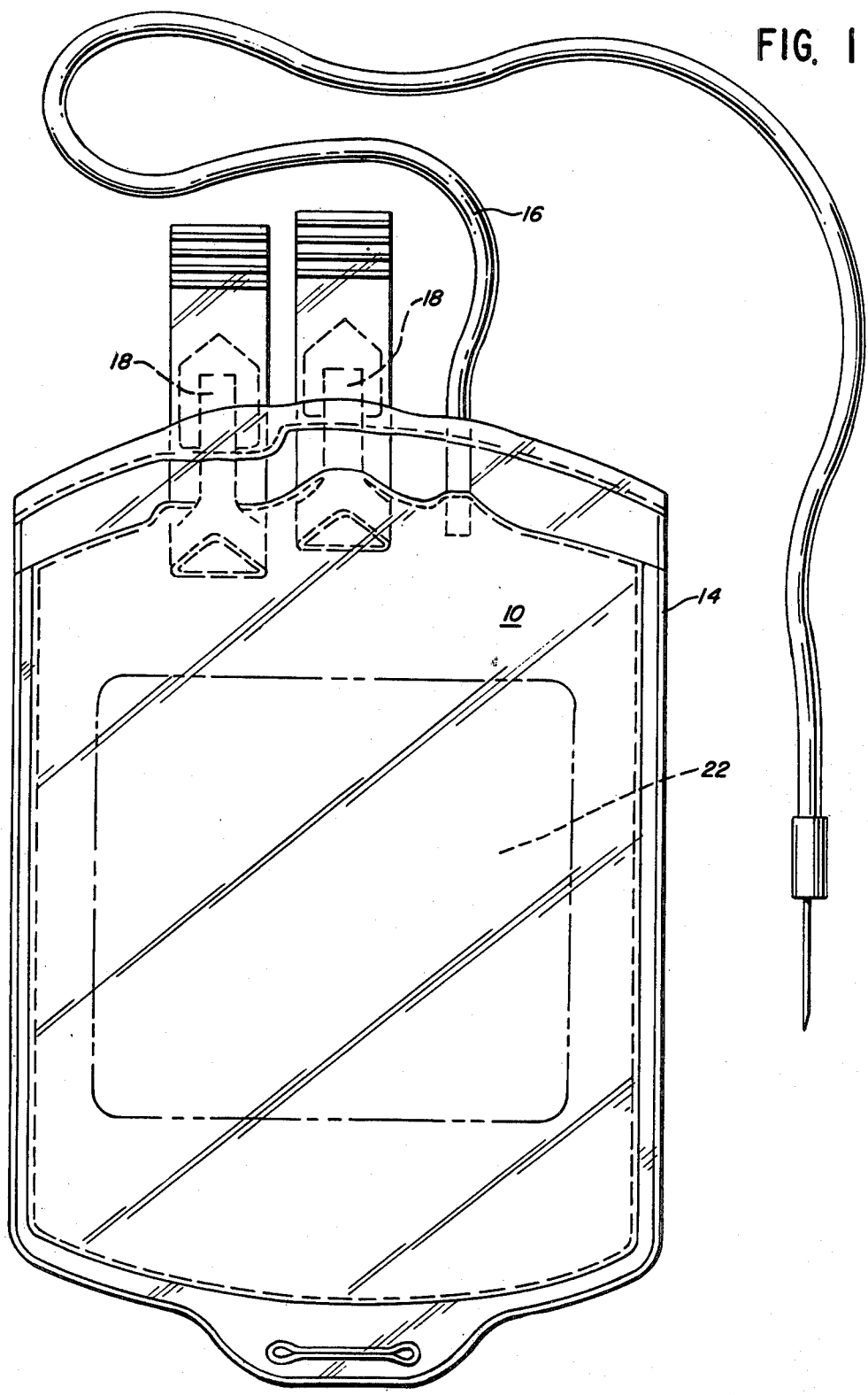

United States Patent [19]

Geissler et al.

[11] 4,451,259
[45] * May 29, 1984

[54] BLOOD STORAGE METHOD

[75] Inventors: Ulrich C. Geissler, Cary; Gerald A. Grode, Grayslake; William J. Stith; Ronald A. Williams, both of Mundelein, all of Ill.

[73] Assignee: Baxter Travenol Laboratories, Inc., Deerfield, Ill.

[*] Notice: The portion of the term of this patent subsequent to Sep. 1, 1998 has been disclaimed.

[21] Appl. No.: 105,469

[22] Filed: Dec. 19, 1979

Related U.S. Application Data

[63] Continuation-in-part of Ser. No. 955,060, Oct. 26, 1978, abandoned.

[51] Int. Cl.³ .............................................. C08K 5/11
[52] U.S. Cl. ..................................... 604/408; 524/297; 524/314
[58] Field of Search ................ 260/31.4, 31.6, 31.8 R, 260/31.8 HR, 31.8 XA, 31.8 F, 31.8 N; 604/408

[56] References Cited

U.S. PATENT DOCUMENTS

| 2,980,964 | 4/1961 | Dilke | 260/31.8 R |
|---|---|---|---|
| 3,308,086 | 3/1967 | Wartman | 260/31.8 R |
| 3,645,955 | 2/1972 | Flynn | 260/31.4 R |
| 3,749,134 | 7/1973 | Slingluff | 260/31.4 R |
| 4,046,725 | 9/1977 | Pusineri | 260/9 |
| 4,076,678 | 2/1978 | Lamb | 260/31.6 |
| 4,085,083 | 4/1978 | Lamb | 260/31.6 |
| 4,286,597 | 9/1981 | Gajewski | 604/408 |
| 4,300,559 | 11/1981 | Gajewski | 128/272 |
| 4,301,800 | 11/1981 | Collins | 128/272 |

Primary Examiner—Paul R. Michl
Attorney, Agent, or Firm—Garrettson Ellis; Paul Flattery

[57] ABSTRACT

Blood-compatible, chlorine-free polymers such as a flexible, non-toxic, sterilizable polyester plastic formulation may contain from 5 to 70 percent by weight of a blood-extractable ester such as di-2-ethylhexylphthalate, to cause blood which is stored in contact with the polymer to exhibit a surprisingly low hemolysis rate when compared with corresponding polymers which are free of the plasticizer. Accordingly, blood bags, tubing and other medical blood-contacting devices may be advantageously made from these polymers.

18 Claims, 1 Drawing Figure

BLOOD STORAGE METHOD

CROSS-REFERENCE TO RELATED APPLICATION

This application is a continuation-in-part of U.S. Application Ser. No. 955,060, filed Oct. 26, 1978, abandoned.

BACKGROUND OF THE INVENTION

Multiple blood bags are commercially available from the Fenwal Division of Baxter Travenol Laboratories, Inc. for collecting and processing blood under sterile conditions, to obtain various blood components that may be desired, for example, packed and red cells, plasma, platelets, and cryoprecipitate.

The currently-available blood bags are made of a polyvinyl chloride formulation which includes, as an ester-type plasticizer, di-2-ethylhexylphthalate. Such a plasticizer is absolutely necessary for polyvinyl chloride formulations, since polyvinyl chloride itself it not a suitable flexible plastic material for use as a container. Such blood bags have served extremely well in the storage and processing of blood and blood components, exhibiting a high survival rate with a low plasma hemoglobin content after, for example, 21 days of storage.

Other chlorine-free plastic formulations have been tested as candidate blood bag materials as well, including flexible polyesters, polyolefins, and the like. Surprisingly, many of the materials tested, while giving indications of being good plastic materials for the manufacture of blood bags, have caused blood stored in containers made of such materials under the usual blood storage conditions to exhibit an undesirably high plasma hemoglobin content after, for example, 21 days of storage, indicating that the lysis rate of the red blood cells is high.

In accordance with this invention, it has been surprisingly found that the presence of certain ester-type plasticizers such as di-2-ethylhexylphthalate and di-2-ethylhexyladipate in various chlorine-free plastics, which do not normally contain such plasticizers when made into blood containers, cause a significant lowering of the plasma hemoglobin content during long-term storage of blood in containers made of such plastic, when compared with containers made of similar plastic materials which are free of the ester-type plasticizers. This can be used to provide blood bags and other blood-contacting medical devices which are made out of chlorine-free plastic entities, having different advantages and properties as may be desired, but which nevertheless exhibit a similar desirably low blood hemolysis rate during long-term storage to that presently available in commercial polyvinyl chloride formulations.

DESCRIPTION OF THE INVENTION

In accordance with this invention, a blood bag or the like may be provided which comprises a sealed, flexible, translucent container equipped with access tubing and sealed access ports. Blood may be stored for a period of 60 days in the bag, which comprises a flexible, hemocompatible, sterilizable, halogen-free plastic formulation which contains, dispersed therein, preferably from 5 to 70 percent by weight of a blood-extractable material comprising a fatty ester containing at least two ester linkages comprising fatty hydrocarbon groups of four to 12 carbon atoms each on a hydrocarbon chain. Specifically, dialkylphthalates, in which each alkyl radical contains from 7 to 10 carbon atoms and having branched chains, is one preferred category of material capable of causing a reduction in the hemolysis of the stored blood, when compared with blood under similar storage conditions in a container free of the blood-extractable materials.

The fatty hydrocarbon groups in the ester linkage

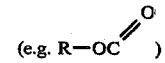

are preferably alkyl radicals of 7 to 10 carbon atoms. The ester linkages are preferably attached to adjacent carbon atoms in the chain, although good results can be obtained from more widely spaced ester groups if the hydrocarbon chain is highly mobile, for example, a saturated, linear hydrocarbon chain as in di-2-ethylhexyladipate.

Examples of the fatty hydrocarbon groups of the ester linkages are the preferred alkyl radicals such as octyl, heptyl, nonyl, decyl, or 2-ethylhexyl. Preferably, the fatty hydrocarbon groups are branched. Other radicals such as hexyl and dodecyl may also be used. Also, similar alkenyl radicals such as octenyl, nonenyl, or decenyl, containing one or more unsaturated linkages, may be used.

Examples of the preferred ester materials are the dioctylphthalates and dioctyladipates, diisononylphthalate, and diisodecylphthalate. Other anti-hemolytic agents which may be used include di-2-ethylhexylmaleate, dibutylphthalate, dihexylphthalate, didodecylphthalate, di-2-ethylhexylazelate, di-2-ethylhexylisophthalate, and di-2-ethylhexylmaleate, all of which exhibit anti-hemolytic properties when in dispersed contact with blood. Emulsions of the ester antihemolytic materials may be added, in accordance with the teachings of the application of Richard G. Buckles, et al. entitled "Anti-Hemolytic Agent Emulsions and the Use Thereof", filed simultaneously with this application.

It is specifically desirable for the concentration and distribution of antihemolytic material in the bag to be such that when the bag is filled with blood and stored on a long-term basis, the concentration of the blood-extractable antihemolytic material in the blood rises to typically about 30 to 100 micrograms per ml., and preferably from 50 to 80 micrograms per ml., in the blood over 21 days. This takes place due to the extraction of the plasticizer from the plastic material in dissolved form into the blood.

It has been found to be generally difficult to dissolve the blood-extractable antihemolytic materials used herein in bulk in the blood. It is found that a greater beneficial effect is provided by placing the extractable materials in the plastic material of the blood bag for extraction by the blood during the storage.

If desired, only portions of the bag materials which are in contact with the blood contained therein may contain the antihemolytic materials of this invention, although preferably the entire bag material contains the antihemolytic material. Alternatively, a plastic insert member such as a sheet of plastic, plastic beads, or the like may be positioned within the blood bag and may contain the antihemolytic material, while the actual bag walls may be relatively free of such material. Both of these circumstances are generally equivalent to the preferred use of blood-extractable antihemolytic material throughout essentially the entire material of the bag.

Preferably, the blood-extractable antihemolytic material used herein may be a branched octylphthalate, and particularly, di-2-ethylhexylphthalate. The blood-extractable material, which also acts as a plasticizer, is preferably present in a concentration in the flexible bag wall of 5 to 50 weight percent and typically about 15 to 40 weight percent.

When a plastic insert is used, the concentration of the blood-extractable antihemolytic material in the insert may be increased up to about 70 percent if desired, since the insert is usually not a structural element and does not have to have a high tensile strength.

The use of the above described blood bag can result in a substantial reduction in plasma hemoglobin produced by blood stored under normal conditions for 21 days therein, when compared with blood in a corresponding bag, free of the anti-hemolytic material and stored under equivalent conditions.

If desired, the formulations of this invention may be used to make medical tubing and other devices.

The materials used in this invention may optionally be a polyester material containing the extractable antihemolytic material in the desired quantity. The polyester material may be made in accordance with the teachings of U.S. Pat. No. 4,045,031.

It may be desirable to incorporate the blood bag of this invention into a multiple bag system containing a plurality of blood bags connected by tubing, in which the additional blood bags may be of similar or different construction from the bag of this invention.

Alternatively, the compositions of this invention, and the resulting bags and medical tubing and similar devices made therefrom, may comprise other halogen-free plastic materials, plasticized as described above with a blood-extractable antihemolytic material such as di-2-ethylhexylphthalate. Candidate polymer materials for this purpose include non-toxic polyurethanes, polyamide materials such as nylon, polycarbonates, polysulfones, polyacrylates, polyvinylacetate and copolymers thereof with other polymer materials such as ethylene polyacrylates, (particularly those of a hydrophilic nature such as hydroxylated polyacrylates), and other plastic materials which are sufficiently compatible with the blood-extractable material used to permit the formation of a stable, solid solution or dispersion of the blood-extractable material in the polymer material.

Referring to the drawings, FIG. 1 is a plan view of a blood bag made in accordance with this invention.

Blood bag 10 may be made of conventional construction, including a pair of plastic sheets sealed at periphery 14 and containing a blood collection tube 16 (which may also be made of the composition of this invention) having the usual donor needle, and a pair of sealed access ports 18.

In accordance with this invention, bag 10 is made of a transparent, flexible, sterilizable and preferably autoclavable material which contains preferably about 20 to 30 percent by weight of a blood-extractable plasticizer and antihemolytic material such as di-2-ethylhexylphthalate. Specifically, the plastic material which contains the blood-extractable plasticizer may be the polyester formulation described above. Such blood bags, which may contain about 20 percent by weight of blood-extractable plasticizer, can cause a substantial reduction in the plasma hemoglobin of blood stored under normal conditions for 21 days in the blood bag, when compared with the corresponding extractable plasticizer-free blood bag made of the same polyester material in which the blood is collected in the bag and stored under equivalent conditions. Such blood bags may be made by soaking the bags in the liquid, blood-extractable plasticizer and antihemolytic material.

If desired an optional plastic insert 22 may be inserted within the bag 10. Insert 22 may be made of a similar material to the bag 10, or a different plastic material which is compatible with the desired blood-extractable plasticizer and antihemolytic material used herein. Accordingly, the material of bag 10 may be relatively free of the desired blood-extractable plasticizer, but insert 22 within the bag may carry any desired amount of the plasticizer, preferably from 15 to 70 percent by weight, to provide the extractable plasticizer to the blood which is placed in bag 10. It has been found that the desirable results of this invention can be achieved by this alternate technique.

Insert 22 may be a single sheet, or a plurality of plastic beads, or any other convenient structure. For example, in this particular alternate instance, blood bag 10 may be made out of a flexible, collapsible plastic material which is generally free of blood-extractable plasticizers, or optionally it may contain such plasticizers as desired. Specific plastic materials with which the blood bag may be made in this instance include the polymers listed above, plus polyolefins such as polyethylene, polypropylene, or polyolefin block copolymer formulations as specifically described in U.S. patent application Ser. No. 819,924, filed July 28, 1977, now U.S. Pat. No. 4,140,162.

Insert 22, on the other hand, may be made of a blood-compatible plastic material including any of the above-listed polymers, for example, a blood-compatible polyvinylchloride formulation which may contain preferably up to about 50 percent di-2-ethylhexylphthalate, or other antihemolytic material, to be extracted into the blood over the storage period. If desired, higher concentrations than 50 percent of the extractable antihemolytic material may be placed in insert 22, since there is no need for insert 22 to exhibit a high tensile strength, as would be necessary if it were part of the bag wall itself.

Bag 10 may contain an appropriate blood preservative such as ACD or CPD solution, as is conventional for storage of the blood. During storage, the presence of the plasticizer effectively suppresses the amount of plasma hemoglobin which is generated over a period of time, compared with blood stored in a bag made of an extractable plasticizer-free plastic formulation. Accordingly, the above described halogen-free plastic formulations may, for the first time, be formulated into blood bags and other medical devices for long-term contact with blood, while at the same time, exhibiting an unexpectedly low red cell hemolysis rate, when compared with the corresponding plasticizer-free plastic formulations.

If desired, blood bag 10 may be equipped with a sterile connector device, for example that shown in U.S. Pat. Nos. 4,004,486 and 4,157,723, or any other sterile connector system, so that the bag may be connected together with other blood bags or sterile equipment without breaching the sterility of the system.

The following examples are for illustrative purposes only, and are not intended to limit the invention described herein.

EXAMPLE 1

Blood bags were prepared of a design similar to the commercially-available Fenwal donor bag, but made of a polyester as described in U.S. Pat. No. 4,045,431. The blood bags were sterilized in accordance with commercial standards, and whole blood was drawn into the blood bags.

The first group of bags was made of the same polyester and was plasticizer-free, while the second group of bags was soaked to about a 20 weight percent concentration of di-2-ethylhexylphthalate plasticizer.

The blood was divided between the first group and second group of bags in equal quantities in a conventional manner, and the bags were sealed off. Thereafter, the bags were stored at 4° C., for 21 days.

Then the amount of plasma hemoglobin was measured in the two groups of bags, with the results as shown in Table I below.

TABLE I

| Multiple Bag Number | Plasma Hemoglobin (mg %) | |
| --- | --- | --- |
| | First Group of Bags (Plasticizer-Free) | Second Group of Bags Containing Plasticizer |
| 1 | 40.7 mg. % | 16.5 mg. % |
| 2 | 36.7 | 21.3 |
| 3 | 11.5 | 7.2 |
| 4 | 21.1 | 9.4 |
| 5 | 20.9 | 12.3 |
| 6 | 42.6 | 9.8 |
| 7 | 62.7 | 21.4 |
| 8 | 34.0 | 18.4 |
| 9 | 44.6 | 14.6 |
| 10 | 31.8 | 9.7 |
| Average | 34.7 | 14.1 |

The above data shows the significant reduction in plasma hemoglobin which results from storing whole blood for 21 days under conventional storage conditions in a blood bag which contains plasticizer, even when the plasticizer is not necessary for its usual purpose of obtaining desired characteristics in the plastic of the blood bag.

The above has been offered for illustrative purposes only and is not intended to limit the invention of this application, which is as defined in the claims below.

That which is claimed is:

1. The method which comprises storing blood for a period of days in a container made from a blood-compatible polymer, said polymer comprising a sterilizable, flexible, chlorine-free plastic material which contains sufficient antihemolytic agent dispersed therethrough to cause a reduced plasma hemoglobin content of the blood stored in contact therewith for 21 days, when compared with blood stored for a similar period of time in contact with the same blood-compatible material free of said antihemolytic agent, said antihemolytic agent comprising a fatty ester containing 2 ester linkages comprising fatty aliphatic hydrocarbon groups of 4 to 12 carbon atoms each, attached to a hydrocarbon chain and separated by no more than 7 carbon atoms.

2. The method of claim 1 in which the ester linkages of said antihemolytic agent comprise alkyl groups of 7 to 10 carbon atoms.

3. The method of claim 2 in which said alkyl groups are branched alkyl groups, and said ester linkages are positioned on adjacent carbon atoms.

4. The method of claim 2 in which the ester groups of said antihemolytic agent contain branched octyl radicals.

5. The method of claim 4 in which said antihemolytic agent is di-2-ethylhexylphthalate.

6. The method of claim 4 in which said antihemolytic agent is diisononylphthalate.

7. The method of claim 4 in which said antihemolytic agent is diisodecylphthalate.

8. The method of claim 1 in which said container includes from 5 to 70 percent by weight of said antihemolytic agent, which also functions as a plasticizer.

9. The method of claim 8 in which said container contains from 15 to 40 percent by weight of said antihemolytic agent.

10. The method of storing blood for over a day into a container made of a blood-compatible polymer which comprises a hemocompatible, flexible sterilizable, chlorine-free plastic material, while providing to said blood in said container a sufficient concentration of a dispersed dialkylphthalate in which said alkyl groups each contain 4 to 12 carbon atoms, to cause a reduced plasma hemoglobin content of blood stored in contact therewith for 21 days, when compared with blood stored in contact with the same blood-compatible material free of said antihemolytic agent.

11. The method of storing blood for over a day into a container made of a blood-compatible polymer which comprises a hemocompatible, flexible sterilizable, chlorine-free plastic material, while providing to said blood in the container a sufficient concentration of dispersed dioctylphthalate to cause a reduced plasma hemoglobin content of blood stored in contact therewith for 21 days, when compared with blood stored in contact with the same blood-compatible material free of dioctylphthalate.

12. The method of claim 11 in which said dioctyl phthalate is di-2-ethylhexylphthalate.

13. The method of storing blood for over a day into a container made of a blood-compatible polymer which comprises a hemocompatible, sterilizable, chlorine-free plastic material, while providing to said blood in said container a sufficient concentration of a dispersed antihemolytic agent to cause a reduced plasma hemoglobin content of blood stored in contact therewith for 21 day, when compared with blood stored in contact with the same blood-compatible material free of said antihemolytic agent said antihemolytic agent comprising a fatty ester containing 2 ester linkages comprising fatty aliphatic hydrocarbon groups of 4 to 12 carbon atoms each on a hydrocarbon chain and separated by no more than 7 carbon atoms.

14. The method of claim 13 in which said ester linkages are spaced on adjacent carbon atoms of said hydrocarbon chain.

15. The method of claim 14 in which the ester linkages of said antihemolytic agent comprise alkyl groups of 7 to 10 carbon atoms.

16. The method of claim 15 in which said alkyl groups are branched alkyl groups.

17. The method of claim 15 in which the ester groups of said antihemolytic agent contain branched octyl radicals.

18. The method of claim 13 in which said hydrocarbon chain is linear and highly mobile.

* * * * *